United States Patent [19]

Shigeno et al.

[11] Patent Number: 5,385,737

[45] Date of Patent: Jan. 31, 1995

[54] SURFACTANT-CONTAINING SEAMLESS CAPSULES

[75] Inventors: Chitoshi Shigeno; Naoki Katada; Jun Shida, all of Wakayama; Norikazu Iwase, Tochigi; Hirotaka Sato, Tochigi; Hidenori Yorozu, Tochigi, all of Japan

[73] Assignee: Kao Corporation, Tokyo, Japan

[21] Appl. No.: 74,414

[22] Filed: Jun. 10, 1993

[30] Foreign Application Priority Data

Jun. 12, 1992 [JP] Japan .................................. 4-179023
Jun. 27, 1992 [JP] Japan .................................. 4-193327

[51] Int. Cl.⁶ .............................................. A61K 9/48
[52] U.S. Cl. .................................. 424/451; 264/4.3; 264/4.33; 252/108
[58] Field of Search ................ 424/451; 264/4.3, 4.33; 252/108

[56] References Cited

FOREIGN PATENT DOCUMENTS

| | | |
|---|---|---|
| 0525731 | 2/1993 | European Pat. Off. |
| 2650758 | 2/1991 | France |
| 53-39193 | 10/1978 | Japan |
| 58-13508 | 1/1983 | Japan |
| 5-31352 | 2/1993 | Japan |
| 675370 | 7/1991 | Switzerland |

OTHER PUBLICATIONS

Patent Abstract of Japan, vol. 12, No. 176, 25 May 1988 & JP-A-62 282 658 (Sankyo K.K.), Dec. 1987.
Patent Abstract, Section Ch, Week 1076, Derwent Publications Ltd., Class B07, An 7617781X & JP-A-51 008 (Morishita Jintan KK) Jan., 1976.
Patent Abstract, Section Ch, Week 1076, Derwent Publications Ltd., Class J04, An 76-17782x & JP-A-51 008 178 (Morishita Jintka KK) Jan., 1976.

*Primary Examiner*—Samuel A. Acquah
*Attorney, Agent, or Firm*—Birch, Stewart, Kolasch & Birch

[57] ABSTRACT

Surfactant-containing seamless capsules of the present invention have an inner layer and an outer layer having a film-forming material. The inner layer contains an oily component and a surfactant component. Such surfactant-containing seamless capsules are produced using in multiple nozzle of triple or more having a sequentially increasing diameter. Since the capsules are excellent in emulsive dispersibility of the content liquid and surfactant dispersibility and solubility in the oily component, they can be used in pharmaceuticals, foods, luxury foods, bath additives, detergents and other fields.

12 Claims, 2 Drawing Sheets

SURFACTANT-CONTAINING SEAMLESS CAPSULES

BACKGROUND OF THE INVENTION

1. Field of the Invention

The present invention relates to surfactant-containing seamless capsules and a method for producing them. More specifically, it relates to seamless capsules containing a surfactant component and an oily component, which can be used in the fields of pharmaceuticals, foods, luxury foods, bath additives and detergents, and to a method for producing such surfactant-containing seamless capsules.

2. Description of the Related Art

There have traditionally been produced seamless capsules containing an oily component, such as a vegetable oil, but no surfactants. This type of seamless capsules is prepared by means of interfacial tension, as disclosed in Japanese Patent Examined Publication No. 3700/1961. Therefore, when the liquid content contains a surfactant component having a high HLB value, the encapsulation has been difficult because of considerable reduction in the interfacial tension between the content liquid and the film-forming liquid.

Japanese Patent Laid-Open Nos. 227519/1986 and 238519/1989 disclose capsules containing a nonionic surfactant having a relatively high HLB value. However, because these capsules are produced by encapsulation using a capsule-filling machine, their film has a seam, which results in problems of leakage of the contents, and dissolution speed variation among capsules due to uneven distribution of mean film thickness, as well as undesirable appearance.

On the other hand, Japanese Patent Examined Publication No. 39193/1978 and Japanese Patent Laid-Open No. 99177/1980 disclose seamless capsules having a multiple-layer structure obtained using a multiple-nozzle, but these capsules contain no surface-active component. Also, Japanese Patent Laid-Open No. 52639/1991 discloses seamless capsules wherein surface-active, lower fatty acid esters of sucrose is present between the hydrophilic substance and the film. However, this disclosure does not deal with capsules containing a surfactant component and an oily component as the content.

Furthermore, Japanese Patent Laid-Open No. 13508/1983 discloses seamless capsules of a pharmaceutical composition containing a dispersion of both a practically water-insoluble drug and a polyglycerol fatty acid ester in a liquid oil. Also, Japanese Patent Laid-Open No. 31352/1993 discloses seamless capsules containing a hydrophilic substance and a method for production thereof. However, these proposals pose problems such as functional reduction due to insufficient adsorption of the oily component to the skin because of its separation from water when the capsules are applied to bath additives and other uses in water. In other words, these publications give no disclosure of capsules wherein the content liquid can be substantially emulsified and dispersed in water, or capsules wherein the surfactant component is substantially uniformly dispersed or dissolved in the oily component, and no disclosure of a method for production thereof.

As stated above, there has not been known any seamless capsules containing a surfactant component and an oily component as the contents of the capsules wherein the liquid content is excellently emulsifiable and dispersible in water or the surfactant component is excellently dispersible or soluble in the oily component, or any method for production of such capsules. In particular, in the fields of bath additives and detergents, where high emulsifiability and dispersibility are required for the liquid content, there has been a need for the development of such seamless capsules and a method for production thereof.

SUMMARY OF THE INVENTION

It is an object of the present invention to provide seamless capsules containing a surfactant component and an oily component wherein the liquid content is excellently emulsifiable and dispersible in water or the surfactant component is excellently dispersible or wherein soluble in the oily component, thereby solving the above problems.

It is another object of the present invention to provide a method for producing such capsules.

Accordingly, the present invention essentially relates to:

(1) Surfactant-containing seamless capsules comprising an inner layer and an outer layer having a film-forming material, wherein said inner layer contains an oily component and a surfactant component, and the emulsifiability of a content liquid in the capsules is such that when 0.5 g of the content liquid is added to 2.5 liters of 40° C. water, followed by stirring under the conditions shown below, the oily component remains emulsified and dispersed and substantially unseparated from the water at 40° C.;

Stirring conditions:

| Container: | Three-liter beaker (14 cm inside diameter, 20 cm height); |
| --- | --- |
| Impeller: | Anchor blade (5 cm diameter, 5 cm height, 1 cm width); |
| Blade position: | Upper side of the blade located 1 cm below the water surface level; |
| Rotational speed of blade: | 150 rpm; and |
| Stirring time: | 30 seconds; |

(2) Surfactant-containing seamless capsules comprising an inner layer and an outer layer having a film-forming material, wherein said inner layer contains an oily component and a surfactant component, the surfactant component being substantially uniformly dispersed or dissolved in the oily component;

(3) A method for producing surfactant-containing seamless capsules using a multiple nozzle of triple or more, having a sequentially increasing diameter, comprising the steps of continuously discharging a film-forming liquid from the outermost nozzle, and an aqueous dispersion containing an oily component and a surfactant component from at least one of the other nozzles to form multiple-layered droplets, and then hardening or gelling the film-forming liquid of the multiple-layered droplets;

(4) A method for producing surfactant-containing seamless capsules using a multiple nozzle of triple or more having a sequentially increasing diameter, comprising the steps of continuously discharging a film-forming liquid from the outermost nozzle, and an aqueous dispersion containing an oily component, a surfactant component and a hydrophilic organic solvent from at least one of the other nozzles to form multiple-layered droplets, and then hardening or gelling the film-forming liquid of the multiple-layered droplets;

(5) A method for producing surfactant-containing seamless capsules using a multiple nozzle of triple or more having a sequentially increasing diameter, comprising the steps of continuously discharging a film-forming liquid from the outermost nozzle, and a non-aqueous liquid comprising an oily component and a surfactant component from at least one of the other nozzles to form multiple-layered droplets, and then hardening or gelling the film-forming liquid of the multiple-layered droplets;

(6) A method for producing surfactant-containing seamless capsules using a multiple nozzle of triple or more having a sequentially increasing diameter, comprising the steps of continuously discharging a film-forming liquid from the outermost nozzle, a surfactant component from at least one of the other nozzles, and an oily component from further at least one of the other nozzles, to form multiple-layered droplets, and then hardening or gelling the film-forming liquid of the multiple-layered droplets; and (7) A bath additive composition comprising surfactant-containing seamless capsules and a bath additive base.

Further scope of applicability of the present invention will become apparent from the detailed description given hereinafter. However, it should be understood that the detailed description and specific examples while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by way of illustration only, and thus, are not limitative of the present invention, and wherein.

The reference numerals in FIGS. 1 and 2 denote the following elements.

Element 1 is the innermost nozzle, element 2 an intermediate nozzle, element 3 the outermost nozzle, element 4 an inlet for the outermost nozzle, element 5 an inlet for the intermediate nozzle, element 6 an inlet for the innermost nozzle, element 7 a three-liter beaker, element 8 a motor, element 9 an anchor blade, "D" a blade diameter (5 cm), "H" a blade height (5 cm), "m" a blade width (1 cm), and "h" a distance between the upper side of the blade and the water surface (1 cm).

DETAILED DESCRIPTION OF THE INVENTION

The surfactant-containing seamless capsules of the present invention (hereinafter also simply referred to as "capsules") are capsules comprising an inner layer and an outer layer. The outer layer has a film-forming material. The inner layer comprises a single layer, or two or more concentric layers, which are formed with an appropriate combination of layers such as (1) a layer comprising an aqueous dispersion containing an oily component and a surfactant component, (2) a layer comprising an aqueous dispersion containing an oily component, a surfactant component and a hydrophilic organic solvent, (3) a non-aqueous liquid layer comprising an oily component and a surfactant component, (4) a layer of an oily component, and (5) a layer of a surfactant component.

Accordingly, the capsules of the present invention are available in various embodiments as follows:

(a) Capsules comprising a single inner layer and an outer layer having a film-forming material, wherein the mentioned inner layer comprises an aqueous dispersion containing an oily component and a surfactant component;

(b) Capsules comprising a single inner layer and an outer layer having a film-forming material, wherein the mentioned inner layer comprises a non-aqueous liquid comprising an oily component and a surfactant component;

(c) Capsules comprising two or more concentric inner layers and an outer layer having a film-forming material, wherein at least one of the mentioned inner layers comprises an aqueous dispersion containing an oily component and a surfactant component;

(d) Capsules comprising two or more concentric inner layers and an outer layer having a film-forming material, wherein at least one of the mentioned inner layers comprises an aqueous dispersion containing an oily component, a surfactant component and a hydrophilic organic solvent;

(e) Capsules comprising two or more concentric inner layers and an outer layer having a film-forming material, wherein at least one of the mentioned inner layers comprises a non-aqueous liquid comprising an oily component and a surfactant component; and (f) Capsules comprising two or more concentric inner layers and an outer layer having a film-forming material, wherein at least one of the mentioned inner layers comprises a surfactant component.

(g) Capsules comprising two or more concentric inner layers and an outer layer having a film-forming material, wherein at least one of the mentioned inner layers comprises an oily component.

Such capsules, comprising two or more concentric inner layers and an outer layer having a film-forming material, are hereinafter described in more detail. For example, capsules comprising three layers, namely an inner layer consisting of an intermediate layer and an innermost layer and an outer layer, include various forms as follows (the following components are contained in the outer layer/inner layer (intermediate layer)/inner layer (innermost layer), respectively).

(1) Hydrophilic film-forming material/oily component/aqueous dispersion containing surfactant component and oily component;

(2) Hydrophilic film-forming material/oily component/aqueous dispersion containing surfactant component, oily component and organic solvent;

(3) Hydrophilic film-forming material/oily component/non-aqueous liquid comprising surfactant component and oily component;

(4) Hydrophilic film-forming material/oily component/surfactant component;

(5) Lipophilic film-forming material/aqueous component/non-aqueous liquid comprising surfactant component and oily component;
(6) Lipophilic film-forming material/surfactant component/oily component;
(7) Lipophilic film-forming material/aqueous dispersion containing surfactant component and oily component/oily component; and
(8) Lipophilic film-forming material/aqueous dispersion containing surfactant component, oily component and organic solvent/oily component.

Components of the layers constituting the capsules of the present invention are described below.

First, the outermost layer is a layer having a film-forming material. The liquid used to form the film is a molten liquid of the film-forming material or a solution containing the film-forming material. Any film-forming material, whether hydrophilic or lipophilic, can be used for this purpose without limitation, as long as it hardens or gels upon a physical treatment, such as cooling, or a chemical treatment, such as a crosslinking reaction. For use in bathing products (e.g., bath additives) and detergent compositions (e.g., body detergents), natural, semi-synthetic or synthetic hydrophilic polymers with high affinity with water are preferably used.

Such film-forming materials include, but are not limited to, natural hydrophilic polymers such as glue, gelatin, collagen protein, casein, sodium alginate, carrageenan, furcelan, tamarind gum pectin, gum arabic, guar gum, xanthane gum, tragaganth gum, locust bean gum, agar and starch; semi-synthetic hydrophilic polymers such as carboxymethyl cellulose, methyl cellulose, hydroxyethyl, cellulose, hydroxypropyl cellulose, cellulose acetate phthalate, alginic acid propylene glycol ester, oxidized starch, esterified starch, etherified starch and cationized starch; and synthetic hydrophilic polymers such as sodium polyacrylate, polyethyleneimine, polyvinyl alcohol, polyethylene oxide and polyvinylpyrrolidone. These hydrophilic polymers may be used singly or in combination.

When a solution containing a film-forming material is used as a film-forming liquid, it is preferable to use a hydrophilic polymer as a 0.1 to 80% by weight solution, more preferably a 1 to 50% by weight solution. Although any solvent can be used without limitation, water is preferred.

In this case, one or more water-soluble polyhydric alcohols or derivatives thereof may be added in combination with the above hydrophilic polymer. When they are added, their amount is normally 5 to 100% by weight, preferably 10 to 80% by weight, based on the amount of film-forming material. Examples of water-soluble polyhydric alcohols and derivatives thereof added include, but are not limited to, glycerol, sorbitol, ethylene glycol, polyethylene glycol, propylene glycol, polypropylene glycol, ethylene oxide-propylene oxide copolymer, oligosaccharides and glycerides.

In the present invention, the lipophilic film-forming materials can also be used for the same purpose, including polystyrene, polymethyl methacrylate, polybutadiene, styrene-butadiene rubber, vinyl acetate-ethylene copolymer, vinylidene chloride-acrylonitrile copolymer, styrene-acrylate copolymer and ethyl cellulose, which may be used singly or in combination. When a solution containing a lipophilic film-forming material is used as a film-forming liquid, any solvent can be used without limitation, as long as it serves as a good solvent for the film-forming material. Such solvents include dichloromethane, chloroform, carbon tetrachloride and benzene.

The inner layer is a layer containing an oily component and a surfactant component which comprises a single layer, or two or more concentric layers. The inner layer is formed with an appropriate combination of layers such as (1) a layer comprising an aqueous dispersion containing an oily component and a surfactant component, (2) a layer comprising an aqueous dispersion containing an oily component, a surfactant component and a hydrophilic organic solvent, (3) a non-aqueous liquid layer comprising an oily component and a surfactant component, (4) a layer of an oily component, and (5) a layer of a surfactant component.

The surfactant used for this purpose is one or more surfactants selected from the group consisting of anionic surfactants, cationic surfactants, nonionic surfactants and amphoteric surfactants, with preference given to surfactants having a high solubility in oils. When two or more surfactants are used, even those having a low solubility in oils can be used, as long as their mixture has a satisfactory solubility as a whole. Also, in applications wherein the liquid content becomes in contact with the skin after capsule disintegration, it is preferable to select one or more nonionic surfactants less irritative to the skin.

Examples of anionic surfactants include, but are not limited to, sodium lauryl sulfate, triethanolamine lauryl sulfate, ammonium lauryl sulfate, sodium dodecylbenzene sulfonate, sodium stearate, semi-hardened beef fatty acid sodium salt, semi-hardened beef fatty acid potassium salt, potassium oleate, castor oil potassium salt, sodium alkylnaphthalene sulfonate, sodium dialkylsulfosuccinate, sodium alkyldiphenylether disulfonate, diethanolamine alkylphosphate, potassium alkylphosphate, sodium polyoxyethylene alkylsulfate, triethanolamine polyoxyethylene alkylether sulfate and sodium polyoxyethylene alkylphenylether sulfate.

Examples of cationic surfactants include, but are not limited to, lauryltrimethylammonium chloride, stearyltrimethylammonium chloride, cetyltrimethylammonium chloride, distearyldimethylammonium chloride, alkylbenzene dimethylammonium chloride, stearylamine oleate, stearylamine acetate and stearylamine acid salt.

Examples of nonionic surfactants include, but are not limited to, glycerol fatty acid esters, propylene glycol fatty acid esters, sorbitan fatty acid esters, polyoxyethylene sorbitan fatty acid esters, propylene fatty acid esters, glycerol fatty acid esters, sucrose fatty acid esters, polyoxyethylene sorbitol fatty acid esters, polyoxyethylene sorbitol tetraoleate, polyoxyethylene alkyl ether, polyoxypropylene alkyl ether, polyoxyethylene polyoxypropylene glycol, polyoxyethylene polyoxypropylene alkyl ether, polyethylene glycol fatty acid esters, polyoxyethylene castor oil and polyoxyethylene hardened castor oil. Of these, sorbitan fatty acid esters, polyoxyethylene sorbitan fatty acid esters and polyoxyethylene sorbitol fatty acid esters are preferred, since their skin irritativity is low.

Examples of amphoteric surfactants include, but are not limited to, betaine alkyldimethylaminoacetate, alkyldimethylamine oxide, alkylcarboxymethyl-hydroxyethyl-imidazolium betaine, lecithin, laurylaminopropionic acid and alkyldiaminoethyl glycine.

To allow good emulsification of the oily component of the content upon capsule disintegration in water, the HLB of the nonionic surfactant for seamless encapsulation is normally 7 to 18, preferably 8 to 18, and more preferably 9 to 18.

Two or more nonionic surfactants can be combined, as long as the HLB value of their mixture is 7 to 18, and a nonionic surfactant having an HLB value of lower than 7 may be added to adjust the HLB in the capsules. The capsules of the present invention are produced by continuously discharging liquids for formation of respective layers, using a multiple nozzle, as described later. The nonionic surfactant having an HLB value of lower than 7 used for HLB adjustment may be added to any of the liquids for the inner layer.

Although the amount of surfactant used is not subject to limitation, the weight ratio of the surfactant component to the oily component in the capsules falls in the range of normally from 1:49 to 32:1 i, preferably from 1:19 to 1:1.5.

Examples of oily components used for the present invention include, but are not limited to, oils and fats, waxes, hydrocarbons, higher fatty acids, higher alcohols, esters, essential oils and silicone oils, which may be preferably used singly or in combination.

Examples of oils and fats include, but are not limited to, natural oils and fats such as soybean oil, rice bran oil, jojoba oil, avocado oil, almond oil, olive oil, cacao fat, sesame oil, persic oil, castor oil, coconut oil, mink oil, beef tallow and lard, hardened oils obtained by hydrogenation of these natural oils and fats, and synthetic triglycerides such as myristic glyceride and 2-ethylhexanoic glyceride. Waxes include carnauba wax, whale wax, yellow beeswax and lanoline. Hydrocarbons include sulfuric paraffin, vaseline, paraffin microcrystalline wax, ceresin, squalane and pristane. Higher fatty acids include lauric acid, myristic acid, palmitic acid, stearic acid, behenic acid, oleic acid, linoleic acid, linolenic acid, lanolic acid and isostearic acid. Higher alcohols include lauryl alcohol, cetyl alcohol, stearyl alcohol, oleyl alcohol, lanoline alcohol, cholesterol and 2-hexyldecanol. Esters include cetyl octanoate, myristyl lactate, cetyl lactate, isopropyl myristate, myristyl myristate, isopropyl palmirate, isopropyl adipate, butyl stearate and decyl oleate. Essential oils include mentha oil, jasmine oil, camphor oil, hinoki oil, tohi oil, rue oil, turpentine oil, cinnamon oil, bergamot oil, citrus oil, calamus oil, pineapple oil, lavender oil, bay oil, clove oil, hiba oil, rose oil, eucalyptus oil, lemon oil, peppermint oil, rose oil, sage oil, menthol, cineol, eugenol, citral, citronellal, borneol, linallol, geraniol, camphor, thymol, spilanthol, pinene, limonene and terpenoid compounds. Silicone oils include dimethylpolysiloxane. These examples are not to be construed as limitative.

In embodiment (1) of the present invention, wherein a layer comprising an aqueous dispersion containing an oily component and a surfactant component is formed, the aqueous dispersion is obtained by a known technique such as direct emulsification of a mixture of one or more oily components in water using one or more surfactants selected from the group consisting of anionic surfactants, cationic surfactants, nonionic surfactants and amphoteric surfactants as described above, or emulsification of the oily component in water via phase inversion from a water-in-oil emulsion to an oil-in-water emulsion. This emulsification is achieved using known means such as various mechanical stirrers and mixers. The surfactant concentration in the aqueous dispersion, subject to no limitation, is normally 10 to 300% by weight, preferably 50 to 250% by weight, based on the amount of the oily component in the aqueous dispersion. Surfactant concentrations of lower than 10% by weight are undesirable, since the oily component of the content does not emulsify upon capsule disintegration in water, and surfactant concentrations exceeding 300% by weight are also undesirable, since they result in an increased viscosity of the aqueous dispersion, which in turn lowers the success rate of capsule formation.

The oily component concentration in the aqueous dispersion, subject to no limitation, is normally 2 to 150% by weight, preferably 5 to 130% by weight, based on the water content. Oily component concentrations exceeding 150% by weight are undesirable, since they result in an increased viscosity of the aqueous dispersion, which in turn lowers the success rate of the capsule formation. Oily component concentrations of lower than 2% by weight are also undesirable, since no stable aqueous dispersion can be obtained.

In embodiment (2) of the present invention, a layer may be formed by adding a hydrophilic organic solvent to the aqueous dispersion of embodiment (1), whereby the viscosity of the aqueous dispersion is reduced, which in turn improves the success rate of the capsule formation when the surfactant concentration in the aqueous dispersion is high. Examples of hydrophilic organic solvents which can be used for this purpose include, but are not limited to, monohydric alcohols such as methanol, ethanol, 1-propanol and 2-propanol, dihydric alcohols such as ethylene glycol, 1,2-propanediol, 1,3-butanediol and 1,5-pentanediol, and ketones such as acetone. These hydrophilic organic solvents may be used singly or in combination.

Here, the hydrophilic organic solvent concentration in the aqueous dispersion, subject to no limitation, is normally 0.01 to 200% by weight, preferably 0.1 to 100% by weight, based on the water content. Hydrophilic organic solvent concentrations of lower than 0.01% by weight are undesirable, since the addition of the hydrophilic organic solvent is not significantly effective in lowering the viscosity of the aqueous dispersion. Hydrophilic organic solvent concentrations exceeding 200% by weight are also undesirable, since the resulting excessively low interfacial tension of the aqueous dispersion hampers spherical particle formation from the aqueous dispersion, which in turn lowers the success rate of capsule formation.

In embodiment (3) of the present invention, wherein a non-aqueous liquid layer comprising an oily component and a surfactant component is formed, the surfactant component and oily component used are the same as those described above. In this case, the oily component concentration, subject to no limitation, is normally 0.01 to 300% by weight, preferably 0.1 to 200% by weight, based on the amount of the surfactant component.

In embodiments (4) and (5) of the present invention, wherein a layer of an oily component and a layer of a surfactant component, respectively, are formed, the oily component and surfactant component used are the same as those described above.

The methods for production of surfactant-containing seamless capsules according to the present invention, using various starting materials as described above, are hereinafter described in detail.

The capsules of the present invention are prepared by continuously discharging a film-forming liquid, from the outermost nozzle and various liquids for the inner layers from the other nozzles to form multiple-layered droplets, by means of a multiple nozzle of triple or more having a sequentially increasing diameter, and subsequently hardening or gelling the film-forming material of the multiple-layered droplets. The liquids discharged from the respective nozzles for the inner layers are the same components as are in the above-described layers of embodiments (1) through (5). Specifically, the liquids include an aqueous dispersion containing an oily component and a surfactant component (first embodiment); an aqueous dispersion containing an oily component, a surfactant component and a hydrophilic organic solvent (second embodiment); a non-aqueous liquid comprising an oily component and a surfactant component (third embodiment); a liquid of an oil component alone (fourth embodiment); and a liquid of a surfactant component alone (fifth embodiment).

For the liquids supplied from nozzles other than the nozzle for discharge of the liquid containing a surfactant component, oily components and aqueous components are appropriately selected under the conditions that encapsulation is not interfered with. For components to be contained in mutually adjoining layers, a combination of components is selected in such a manner that they are substantially immiscible or sparingly miscible with each other such as an oily component and an aqueous component. In this case, the same oily components as described above can be used. Aqueous components which can be used include water, aqueous acetone solutions and aqueous lower alcohol solutions. Examples of combinations of liquids discharged from respective nozzles include (1) through (8) described above.

Figure 1:
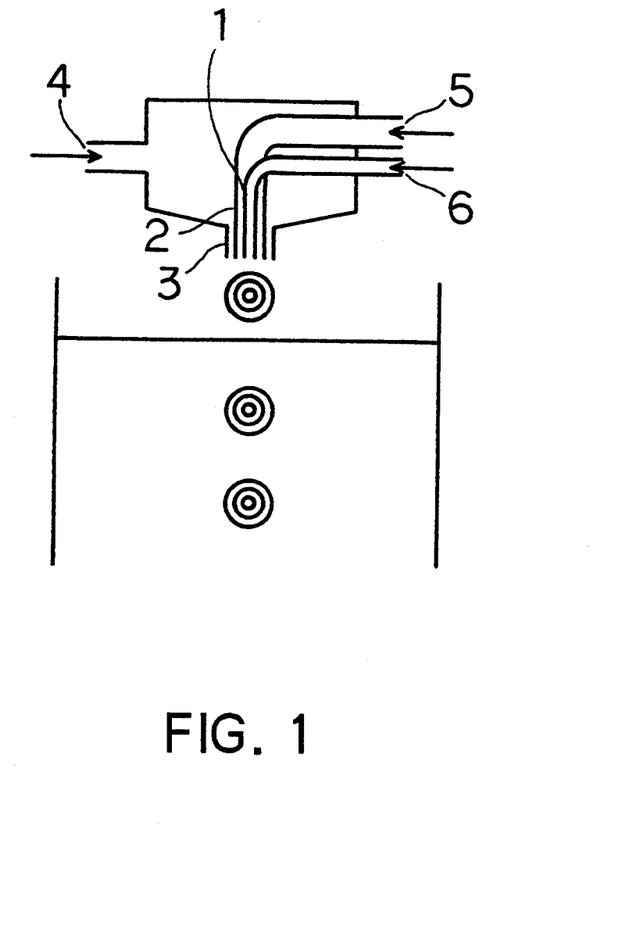
FIG. 1 is a cross-sectional view schematically showing an example of the nozzle portion of a production apparatus used for the production method of the present invention.

FIG. 1 is a cross-sectional view schematically showing an example of the nozzle portion of a production apparatus used for the production method of the present invention. Although FIG. 1 illustrates a triple nozzle with regularly aligned outlet tips, the nozzle is not subject to limitation as to shape etc., as long as it is a multiple nozzle of triple or more having a sequentially increasing diameter. However, the present invention is also directed to, nozzle outlet tips which are aligned differently.

In the production method of the present invention using such a triple nozzle, for example, the film-forming liquid described above, an oily component and a liquid containing a surfactant component are respectively supplied to the nozzle from the inlet 4 for the outermost nozzle, from the inlet 5 for the intermediate nozzle, and from the inlet 6 for the innermost nozzle, and are continuously discharged in a gas or liquid phase via outermost nozzle 3, intermediate nozzle 2 and innermost nozzle 1, respectively, to form multiple-layered droplets. In this case, any liquid phase can be used without limitation, as long as it is substantially immiscible with, or insoluble in, the film-forming material, but a hardener or gelling agent as described later is preferred from the viewpoint of production efficiency. Next, the film-forming liquid of the multiple-layered droplets is hardened or gelled by means of physical or chemical methods to form surfactant-containing seamless capsules. Here, physical means include the method wherein the film-forming liquid is hardened by cooling in contact with a cooled hardener. Chemical means include the method wherein the film-forming liquid is gelled by chemical reaction with a hardener. However, physical or chemical means are not limited to these methods, as long as the film-forming liquid is hardened or gelled.

Although any hardener can be used without limitation, as long as it is a liquid capable of physically or chemically hardening or gelling the film-forming liquid, a substance which is substantially insoluble both in the film-forming liquid and in the film obtained by hardening is appropriately used, when hardening is achieved by cooling. For example, for a hydrophilic film-forming material, one or more oils are selected from the group consisting of oils and fats, waxes, hydrocarbons, higher fatty acids, higher alcohols, esters, essential oils and silicone oils. For a lipophilic film-forming material, water, methanol, ethanol, 1-propanol, 2-propanol and mixtures thereof are used. Cooling temperature is also subject to no limitation, as long as it allows the film-forming liquid to harden.

In the case where the film-forming liquid is gelled chemically, an aqueous solution containing calcium chloride or calcium phosphate for sodium alginate; an aqueous solution containing borax, formalin or hydrochloric acid for polyvinyl alcohol; an aqueous solution containing calcium chloride or zirconium nitrate for gelatin, are appropriately selected; and crosslinking and other reactions of the film-forming liquid with these hardeners result in gelation.

In the production method of the present invention, respective liquids are discharged from a multiple nozzle to form multiple-layered droplets, as stated above. In this operation, capsule diameter can be controlled by total liquid flow rate, liquid viscosity, liquid interfacial tension, frequency as described later, and other factors. Once this capsule diameter is determined, average film thickness can be controlled by the flow rate ratio of the flow rate from the outermost nozzle to the total flow rate from the other nozzles. In this case, average film thickness t can be calculated using the following equation:

$$t = \frac{D - D_1}{2} = \left( \sqrt[3]{\frac{6}{\pi} (V_2 + V_1)} - \sqrt[3]{\frac{6}{\pi} V_1} \right) / 2$$

wherein
  t: Average film thickness [cm];
  D: Average capsule diameter [cm];
  $D_1$: Average capsule inner layer diameter [cm];
  $V_1$: Capsule inner layer volume $[cm^3] = W_1/\rho_1 = Q_1/I$;
  $V_2$ Capsule film volume $[cm^3] = W_2/\rho_2 = Q_2/I$;
  $W_1$: Capsule inner layer weight [g];
  $W_2$: Capsule film weight [g];
  $Q_1$: Total flow rate of inner layer liquids from the nozzle [cm³/min];
  $Q_2$: Flow rate of film-forming liquid from the nozzle [cm³/min];
  $\rho_1$: Average density of inner layer liquids [g/cm³];
  $\rho_2$: Density of film-forming liquid [g/cm³]; and
  I: Number of capsules produced [/min].

In the present invention, liquids are continuously discharged from the respective nozzles of the multiple nozzle to form multiple-layered droplets, as stated above. In this operation, capsule diameter, film thickness, etc. can be made more uniform by vibrating the multiple-layered liquid column being discharged from the multiple nozzle. For this purpose, any known vibrator can be used, and the method for vibration is not subject to limitation. For example, the nozzle may be vibrated, or a liquid flowing into the nozzle may be pulsated, or the outer phase of the multiple-layered liquid column discharged from the nozzle may be vibrated. Frequency of vibration of the multiple-layered liquid column is appropriately selected according to the linear velocity of the liquid column and the liquid viscosity used. On the basis of their relationship with frequency, flow rate discharged from nozzles, and other factors, capsule diameter can be controlled. Required frequency, subject to no limitation, is normally 1 to 3000 Hz, preferably 1 to 2000 Hz, and more preferably 1 to 1000 Hz, from the viewpoint of capsule formation productivity and capsule size uniformity. Frequencies of lower than 1 Hz result in insufficient vibration; frequencies exceeding 3000 Hz result in non-uniformities of capsule size. In the present invention, liquid drops may be also obtained without vibration.

In the present invention, concerning the linear velocity of the liquids discharged from the respective nozzles of the multiple nozzle, the maximum linear velocity is preferably 1.0 to 1.3 times, more preferably 1.0 to 1.1 times, and still more preferably 1.0 to 1.05 times, the minimum linear velocity.

Maximum-to-minimum linear velocity ratios of 1.0 to 1.3 facilitate formation of concentric capsules, resulting in a uniform film thickness. Also, capsules containing a large amount of content liquid can be stably produced by appropriately selecting respective nozzle diameters so that the maximum-to-minimum linear velocity ratios of liquids discharged from the respective nozzles fall in the above range. This also facilitates capsule formation from a combination of starting materials having a low interfacial tension, and also increases success rate of capsule formation by vibrating the multiple-layered liquid column.

Also, in the present invention, in cases where the fluidity, non-caking property and other physical properties of the capsules are deteriorated by the interaction between the water in the capsules and the film-forming material, the surfactant-containing seamless capsules can be dried to remove the water therefrom. In this case, the water content in the capsules can be adjusted as necessary by known drying methods such as hot air drying, vacuum drying and freeze drying. Water can be removed from the capsules by extraction, followed by drying. In the present invention, said water content is normally not more than 25% by weight, preferably not more than 20% by weight, and more preferably not more than 15% by weight. Water contents exceeding 25% by weight are undesirable for capsule use as dry particles because of high tackiness on the capsule surface.

In the present invention, the obtained capsules may be further subjected to extraction and removal of water using a hydrophilic organic solvent. This treatment makes it possible to remove water from the capsules in shorter times than with other methods, and facilitates obtaining wrinkle-free, hollow-free capsules with beautiful film surfaces.

Hydrophilic organic solvents which can be used to remove water by this method include, but are not limited to, monohydric alcohols such as methanol, ethanol, 1-propanol and 2-propanol, and ketones such as acetone, which may be used singly or in combination.

Also, to prevent forming wrinkles during drying, water may be added to the hydrophilic organic solvent used. The amount of water added is normally 2.5 parts by weight or less, preferably 1.0 part by weight or less, and more preferably 0.5 parts by weight or less, relative to 1 part of the hydrophilic organic solvent. Addition of water in amounts of 2.5 parts or more tends to result in deformed capsules.

In comparison with known methods based on drying etc., the method described above can promote water removal from capsules while the capsules remain free of wrinkles and hollows, with more beautiful film surface. In the present invention, to further promote water removal from capsules while the capsules remain free of wrinkles and hollows with more beautiful film surfaces, the water content in the hydrophilic organic solvent may be gradually lowered as the water is removed from the capsules. In addition, to control the drying speed, a hydrophobic organic solvent or a hydrophobic organic solvent and water may be appropriately added to the hydrophobic organic solvent.

The water extracting temperature is normally 1° to 40° C., preferably 5° to 30° C., and more preferably 10° to 20° C. Water extracting temperatures of lower than 1° C result in poor efficiency of water removal from the capsules. Water extracting temperatures exceeding 40° C. are likely to result in deformed capsules.

The amount of hydrophilic organic solvent used is normally 0.5 to 50 parts by weight, preferably 0.7 to 30 parts by weight, and more preferably 1 to 10 parts by weight, relative to 1 part by weight of capsules containing water to be removed. Amounts of lower than 0.5 parts by weight tend to cause mutual adhesion of capsules. Amounts exceeding 50 parts by weight hamper industrially efficient extraction.

This extraction is achieved by a known solid-liquid extraction procedure. The method for extraction is appropriately selected from known methods, such as batch extraction, batch multiple-stage extraction, and continuous counter-current extraction.

The physical properties, emulsification property and other properties of the capsules of the present invention thus obtained are hereinafter described in detail.

In the present invention, the film ratio, i.e., the ratio of film weight to capsule weight, is normally 5 to 60% by weight, preferably 10 to 50% by weight, and more preferably 13 to 40% by weight, from the viewpoint of capsule stability during storage and capsule disintegrability in water, such as in a bath.

The average particle diameter of the capsules of the present invention, subject to no limitation, is normally 0.2 mm to 2 cm, and from the viewpoint of productivity, preferably 3 mm to 2 cm. This is because productivity per multiple nozzle increases as the average particle diameter increases when capsules are produced using, for example, the multiple nozzle described below. The average particle diameter is expressed by weight.

The average film thickness of the capsules, subject to no limitation, is normally 0.01 mm to 5 mm, preferably 0.03 mm to 1 mm. Here, the average film thickness is measured by a known measuring technique, e.g., a micrometer.

The capsules of the present invention are excellent in emulsifiability, possessing the following emulsification property as determined by an emulsifiability test.

Specifically, 0.5 g of the liquid content is added to 2.5 liters of 40° C. water, followed by stirring under the following conditions to emulsify and disperse the oily component in the inner layer. Thereafter, the dispersion is observed with the naked eye at 40° C., preferably after being kept standing at 40° C. for 3 hours, more preferably after being kept standing at 40° C. for 6 hours, and particularly preferably after being kept standing at 40° C for 12 hours. It is found that the emulsion phase shows almost no separation, and is substantially unseparated from the water.

Stirring conditions:
Container: Three-liter beaker (14 cm inside diameter, 20 cm height);
Impeller: Anchor blade (5 cm diameter, 5 cm height, 1 cm width);
Blade position: Upper side of the blade located 1 cm below the water surface level;
Rotational speed of blade: 150 rpm; and
Stirring time: 30 seconds.

Therefore, in the present invention, the phrase that the oily component remains emulsified and dispersed and substantially unseparated from the water means that the emulsion phase shows almost no separation without water phase formation in the emulsifiability test, or that the oily component or the mixture of the oily component and the surfactant component is not present in water in the form of oil drops freed from the emulsive dispersion. Also, the capsules of the present invention are characterized in that the surfactant component contained in the inner layer is substantially uniformly dispersed or dissolved in the oily component. This means that when 5 g of the content liquid is taken out from the capsules, transferred to a test tube and kept standing in an atmosphere at 25° C. and 60% relative humidity for 6 hours, the oily component and the surfactant component do not separate from each other.

As stated above, according to the present invention, capsules having a seamless film and containing a surfactant component and an oily component can be provided. Said capsules are also desirable from the viewpoint of appearance, and have a sharp particle diameter distribution, an uniform film thickness and an excellent solubility. Also, since the capsules of the present invention are excellent in emulsive dispersibility of the content liquid and surfactant dispersibility and solubility in the oily component, they can be used in pharmaceuticals, foods, luxury foods, bath additives, detergents and other fields. Moreover, according to various uses, useful components, additives, etc. may be appropriately formulated to provide various functions for the surfactant-containing seamless capsules, which can be used in these fields.

In particular, when the capsules of the present invention are used in bath additives, they serve well, since oily components effective on the skin can be emulsified and dispersed with surfactants. For example, the capsules themselves may be singly used as a bath additive, or may be used as a component of the bath additive composition containing a granular and/or powder bath additive base. Although the starting materials for the granular and/or powder bath additive base vary depending on the desired indications and efficacy of the bath additive composition, one or more components are appropriately selected from the group consisting of inorganic salts, inorganic acids, organic acids, crude drugs, dyes, vitamins, flavors, etc., and used in combination. In other words, such a bath additive composition can be prepared by formulating the above-described capsules encapsulating an oily component and a surfactant component, as a bath additive component, in the granular and/or powder bath additive base. The amount of capsules formulated is normally 0.1 to 99%, preferably 0.5 to 80%. Also, it is preferable to formulate the inorganic acids at 99.9 to 1%, preferably 99.5 to 20%.

These starting materials are exemplified as follows: Inorganic salts include sodium chloride, sodium hydrogen carbonate, sodium carbonate, borax, sodium sulfate, sodium sulfide, sodium sesquicarbonate, sodium nitrate, sodium thiosulfate, sodium polyphosphate, sodium phosphate, calcium oxide, magnesium oxide, calcium carbonate, magnesium carbonate, potassium chloride, potassium sulfide, aluminum sulfate and alum. Inorganic acids include boric acid, metasilicic acid and silicic anhydride. Organic acids include succinic acid, fumaric acid, malic acid, tartaric acid, citric acid and benzoic acid. Crude drugs include fennel, philaodendron bark, chamomile flower, cinnamon, safflower, peony root, ginger. calamus, conidium rhizome, Japanese angelica root, citrus unshiu peel, atractylodes lancea rhizome, Japanese valerian, angelica dahurica root, angelicae radix, mentha herb, hoelen and ginseng. Dyes include various dyes designated by a Ministerial Ordinance of the Ministry of Health and Welfare of Japan, and natural dyes approved as food additives such as chlorophyll, riboflavin, crocin, safflower and anthraquinone. Vitamins include vitamin A, vitamin C, vitamin D and vitamin E. Others include various flavors, sulfur, sinters, mineral sand, mica powder, neutral clay, parched rice bran, fungicides, preservatives and other pharmaceutically necessary components.

EXAMPLES

The present invention is hereinafter described in more detail by means of the following working examples, comparative examples and test examples, but the present invention is not limitative to these examples. FIG. 1 is a cross-sectional view schematically showing the nozzle portion of a triple nozzle having a sequentially increasing diameter, used in the following examples.

EXAMPLE 1

Using an apparatus equipped with a triple nozzle having a sequentially increasing diameter (the innermost nozzle diameter 0.9 mm, the intermediate nozzle diameter 2 mm, and the outermost nozzle diameter 3.5 mm), multiple-layered droplets are prepared by the following method.

Specifically, an aqueous dispersion (average HLB=10.3) prepared by mixing 6% by weight of tri(caprylic acid capric acid)glycerol (Coconard MT, manufactured by Kao Corporation), 12.6% by weight of polyoxyethylene (average adduct molar number 20) sorbitan trioleate (HLB=11) and 1.4% by weight of sorbitan sesquioleate (HLB=3.7), and further adding 80% by weight of water thereto, from the innermost nozzle at a flow rate of 2.2 g/min, tri(capric acid capric acid)glycerol from the intermediate nozzle at a flow rate of 4.4 g/min, and an aqueous solution kept at 70° C. comprising 30% by weight of gelatin, 4% by weight of glycerol and 66% by weight of water, from the outermost nozzle at a flow rate of 5.8 g/min, are simultaneously discharged into a gas phase to form multiple-layered droplets. The resulting droplets are added dropwise to liquid paraffin cooled at 2° C to obtain capsules having a weight ratio of the surfactant component to the oily component of 1:4. The resulting capsules are surfactant-containing seamless capsules comprising two concentric inner layers, namely, the innermost layer comprising an aqueous dispersion containing an oily component and a surfactant component, and the intermediate layer comprising an oily component; and the outermost layer containing a film-forming material.

Using calipers, the average particle diameter D of the capsules is determined to be 5.1 mm, with a coefficient of variance of 6.3% for particle diameter distribution. The average film thickness t is 1.5 mm, as measured using a micrometer. The film ratio is 41.7% by weight.

EXAMPLE 2

The surfactant-containing seamless capsules prepared in Example 1 are cooled in liquid paraffin at 4° C. in the refrigerator for 12 hours and then dried for 12 hours under the conditions of 21° C. and 60% relative humidity to obtain capsules having a weight ratio of the surfactant component to the oily component of 1:4. The resulting capsules are surfactant-containing seamless capsules comprising a single inner layer, which substantially comprises an oily component and a surfactant component, and the outermost layer containing a film-forming material.

Using calipers, the average particle diameter D of the capsules is determined to be 4.2 mm, with a coefficient of variance of 6.6% for particle diameter distribution. The average film thickness t is 0.29 mm, as measured using a micrometer. Also, the water content in the capsule is 3.5% by weight. The film ratio is 25.3% by weight.

EXAMPLE 3

Using an apparatus equipped with a triple nozzle having a sequentially increasing diameter (the innermost nozzle diameter 0.9 mm, the intermediate nozzle diameter 2 mm, and the outermost nozzle diameter 3.5 mm), multiple-layered droplets are prepared by the following method.

Specifically, a mixture (average HLB=10.3) of 20% by weight of tri(caprylic acid capric acid)glycerol, 72% by weight of polyoxyethylene (average adduct molar number 20) sorbitan trioleate (HLB=11) and 8% by weight of sorbitan sesquioleate (HLB=3.7), from the innermost nozzle at a flow rate of 0.2 g/min, tri(caprylic acid capric acid)glycerol from the intermediate nozzle at a flow rate of 0.6 g/min, and an aqueous solution kept at 70° C. comprising 30% by weight of gelatin, 4% by weight of glycerol and 66% by weight of water, from the outermost nozzle at a flow rate of 1.1 g/min, are simultaneously discharged into a gas phase to form multiple-layered droplets. The resulting droplets are added dropwise to liquid paraffin cooled at 2° C. to obtain capsules having a weight ratio of the surfactant component to the oily component of 1:4. The resulting capsules are surfactant-containing seamless capsules comprising two concentric inner layers, namely, the innermost layer comprising an oily component; and a surfactant component and the intermediate layer comprising an oily component; and the outermost layer containing a film-forming material.

Using calipers, the average particle diameter D of the capsules is determined to be 4.8 mm, with a coefficient of variance of 7.2% for particle diameter distribution. The average film thickness t is 0.9 mm, as measured using a micrometer. The film ratio is 57.9% by weight.

EXAMPLE 4

Using an apparatus equipped with a triple nozzle having a sequentially increasing diameter (the innermost nozzle diameter 0.9 mm, the intermediate nozzle diameter 2 mm, and the outermost nozzle diameter 3.5 mm), multiple-layered droplets are prepared by the following method.

Specifically, a mixture (average HLB=10.3) of 90% by weight of polyoxyethylene (average adduct molar number 20) sorbitan trioleate (HLB=11) and 10% by weight of sorbitan sesquioleate (HLB=3.7), from the innermost nozzle at a flow rate of 0.3 g/min, tri(caprylic acid capric acid)glycerol from the intermediate nozzle at a flow rate of 1.2 g/min, and an aqueous solution kept at 70° C. comprising 30% by weight of gelatin, 4% by weight of glycerol and 66% by weight of water, from the outermost nozzle at a flow rate of 1.8 g/min, are simultaneously discharged into a gas phase to form multiple-layered droplets. The resulting droplets are added dropwise to liquid paraffin cooled at 2° C. to obtain capsules having a weight ratio of the surfactant component to the oily component of 1:4. The resulting capsules are surfactant-containing seamless capsules comprising two concentric inner layers, namely, the innermost layer comprising a surfactant component and the intermediate layer comprising an oily component; and the outermost layer containing a film-forming material.

Using calipers, the average particle diameter D of the capsules is determined to be 4.6 mm, with a coefficient of variance of 8.0% for particle diameter distribution. The average film thickness t is 0.9 mm, as measured using a micrometer. The film ratio is 54.6% by weight.

EXAMPLE 5

Using an apparatus equipped with a triple nozzle having a sequentially increasing diameter (the innermost nozzle diameter 0.9 mm, the intermediate nozzle diameter 2 mm, and the outermost nozzle diameter 3.5 mm), multiple-layered droplets are prepared by the following method.

Specifically, a hydrophilic organic solvent-containing aqueous dispersion (average HLB=10.3) prepared by mixing 6% by weight of tri(caprylic acid capric acid)glycerol (Coconard MT, manufactured by Kao Corporation), 12.6% by weight of polyoxyethylene (average adduct molar number 20) sorbitan trioleate (HLB=11) and 1.4% by weight of sorbitan sesquioleate (HLB=3.7), adding 70% by weight of water thereto and further adding 10% by weight of ethanol thereto, from the innermost nozzle at a flow rate of 2.2 g/min, tri(caprylic acid capric acid)glycerol from the intermediate nozzle at a flow rate of 4.4 g/min, and an aqueous solution kept at 70° C. comprising 30% by weight of gelatin, 4% by weight of glycerol and 66% by weight of water, from the outermost nozzle at a flow rate of 5.8 g/min, are simultaneously discharged into a gas phase to form multiple-layered droplets. The resulting droplets are added dropwise to liquid paraffin cooled at 2° C. to obtain capsules having a weight ratio of the surfactant component to the oily component of 1:4. The resulting capsules are surfactant-containing seamless capsules comprising two concentric inner layers, namely, the innermost layer comprising an aqueous dispersion containing an oily component, a surfactant component and a hydrophilic organic solvent, and the intermediate layer comprising an oily component; and the outermost layer containing a film-forming material.

Using calipers, the average particle diameter D of the capsules is determined to be 5.2 mm, with a coefficient of variance of 6.1% for particle diameter distribution. The average film thickness t is 1.5 mm, as measured using a micrometer. The film ratio is 41.7% by weight.

EXAMPLE 6

Using an apparatus equipped with a triple nozzle having a sequentially increasing diameter (the innermost nozzle diameter 0.9 mm, the intermediate nozzle diameter 2 mm, and the outermost nozzle diameter 3.5 mm), multiple-layered droplets are prepared by the following method.

Specifically, a hydrophilic organic solvent-containing aqueous dispersion (average HLB=10.3) prepared by mixing 6% by weight of tri(caprylic acid captic acid)glycerol (Coconard MT, manufactured by Kao Corporation), 12.6% by weight of polyoxyethylene (average adduct molar number 20) sorbitan trioleate (HLB=11) and 1.4% by weight of sorbitan sesquioleate (HLB=3.7), adding 70% by weight of water thereto, and further adding 10% by weight of ethanol thereto, from the innermost nozzle at a flow rate of 4.4 g/min, tri(caprylic acid capric acid)glycerol from the intermediate nozzle at a flow rate of 8.8 g/min, and an aqueous solution kept at 70° C. comprising 30% by weight of gelatin, 4% by weight of glycerol and 66% by weight of water, from the outermost nozzle at a flow rate of 11.6 g/min, are simultaneously discharged into a gas phase while vibrating the nozzle at 10 Hz to form multiple-layered droplets. The resulting droplets are added dropwise to liquid paraffin cooled at 2° C. to obtain capsules having a weight ratio of the surfactant component to the oily component of 1:4. The resulting capsules are surfactant-containing seamless capsules comprising two concentric inner layers, namely, the innermost layer comprising an aqueous dispersion containing an oily component, a surfactant component and a hydrophilic organic solvent, and the intermediate layer comprising an oily component; and the outermost layer containing a film-forming material.

Using calipers, the average particle diameter D of the capsules is determined to be 4.5 mm, with a coefficient of variance of 4.8% for particle diameter distribution. The average film thickness t is 0.3 mm, as measured using a micrometer. The film ratio is 41.7% by weight.

EXAMPLE 7

Using an apparatus equipped with a triple nozzle having a sequentially increasing diameter (the innermost nozzle diameter 0.9 mm, the intermediate nozzle diameter 2 mm, and the outermost nozzle diameter 3.5 mm), multiple-layered droplets are prepared by the following method.

Specifically, an aqueous dispersion (average HLB=10.3) prepared by mixing 6% by weight of tri(caprylic acid captic acid)glycerol (Coconard MT, manufactured by Kao Corporation), 12.6% by weight of polyoxyethylene (average adduct molar number 20) sorbitan trioleate (HLB=11) and 1.4% by weight of sorbitan sesquioleate (HLB=3.7), and adding 80% by weight of water thereto, from the innermost nozzle at a flow rate of 2.2 g/min, tri(caprylic acid captic acid)glycerol from the intermediate nozzle at a flow rate of 4.4 g/min, and a 0.8% by weight aqueous solution of sodium alginate, from the outermost nozzle at a flow rate of 5.8 g/min, are simultaneously discharged into a gas phase to form multiple-layered droplets. The resulting droplets are added dropwise to 3% by weight aqueous solution of calcium chloride to obtain capsules having a weight ratio of the surfactant component to the oily component of 1:4. The resulting capsules are surfactant-containing seamless capsules comprising two concentric inner layers, namely, the innermost layer comprising an aqueous dispersion containing an oily component and a surfactant component, and the intermediate layer comprising an oily component; and the outermost layer containing a film-forming material.

Using calipers, the average particle diameter D of the capsules is determined to be 5.1 mm, with a coefficient of variance of 6.4% for particle diameter distribution. The average film thickness t is 1.5 mm, as measured using a micrometer. The film ratio is 41.7% by weight.

EXAMPLE 8

Using an apparatus equipped with a triple nozzle having a sequentially increasing diameter (the innermost nozzle diameter 0.9 mm, the intermediate nozzle diameter 2 mm, and the outermost nozzle diameter 3.5 mm), multiple-layered droplets are prepared by the following method.

Specifically, tri(caprylic acid captic acid)glycerol from the innermost nozzle at a flow rate of 4.4 g/min, an aqueous dispersion (average HLB=10.3) prepared by mixing 6% by weight of tri(caprylic acid capric acid)glycerol (Coconard MT, manufactured by Kao Corporation), 12.6% by weight of polyoxyethylene (average adduct molar number 20) sorbitan trioleate (HLB=11) and 1.4% by weight of sorbitan sesquioleate (HLB=3.7), and adding 80% by weight of water thereto, from the intermediate nozzle at flow rate of 2.2 g/min, and a non-aqueous solution of 12% by weight of polystyrene in dichloromethane, from the outermost nozzle at a flow rate of 5.8 g/min, are simultaneously discharged into a gas phase to form multiple-layered droplets.

The resulting droplets are added dropwise to water at obtain capsules having a weight ratio of the surfactant component to the oily component of 1:4. The resulting capsules are surfactant-containing seamless capsules comprising two concentric inner layers, namely, the innermost layer comprising an oily component, and the intermediate layer comprising an aqueous dispersion containing an oily component and a surfactant component; and the outermost layer containing a film-forming material.

Next, the obtained suspensions containing the mentioned capsules are heated to 50° C. at a reduced pressure of 100 Torr for 2 hours to remove dichloromethane in the film. Thereafter, using calipers, the average particle diameter D of the capsules is determined to be 4 mm, with a coefficient of variance of 7.8% for particle diameter distribution. The average film thickness t is 0.2 mm, as measured using a micrometer. The film ratio is 7.9% by weight.

EXAMPLE 9

Using an apparatus equipped with a triple nozzle having a sequentially increasing diameter (the innermost nozzle: inner diameter 2 mm and outer diameter 2.2 mm; the intermediate nozzle: inner diameter 2.5 mm and outer diameter 2.7 mm; and the outermost nozzle: inner diameter 3.5 mm), multiple-layered droplets are prepared by the following method.

Specifically, an aqueous dispersion (average HLB=10.3) prepared by mixing 6.6% by weight of tri(caprylic acid capric acid)glycerol (Coconard MT, manufactured by Kao Corporation), 10.5% by weight of polyoxyethylene (average adduct molar number 20) sorbitan trioleate (HLB=11) and 1.2% by weight of sorbitan sesquioleate (HLB=3.7), and adding 81.7% by weight of water thereto, from the innermost nozzle at a flow rate of 1.4 g/min and a linear velocity of 0.45 m/min, tri(caprylic acid capric acid)glycerol from the intermediate nozzle at a flow rate of 0.55 g/min and a linear velocity of 0.53 m/min, and an aqueous solution comprising 30% by weight of gelatin, 4% by weight of glycerol and 66% by weight of water, dissolved at 70° C. and then cooled to 45° C., from the outermost nozzle at a flow rate of 2.193 g/min and a linear velocity of 0.52 m/min, are simultaneously discharged into a liquid phase comprising liquid paraffin cooled at 2° C. to form multiple-layered droplets and obtain capsules having a weight ratio of the surfactant component to the oily component of 1:4. The resulting capsules are surfactant-containing seamless capsules comprising two concentric inner layers, namely, the innermost layer comprising an aqueous dispersion containing an oily component and a surfactant component, and the intermediate layer comprising an oily component; and the outermost layer containing a film-forming material. In the above conditions, the maximum linear velocity of the liquids discharged from each nozzle is 1.18 times the minimum linear velocity thereof.

Using calipers, the average particle diameter D of the capsules is determined to be 7.5 mm, with a coefficient of variance of 6.0% for particle diameter distribution. The average film thickness t is 1.2 mm, as measured using a micrometer. The film ratio is 47% by weight.

EXAMPLE 10

Surfactant-containing seamless capsules prepared in Example 1 (capsule water content=48.7% by weight) are added to a two times greater weight of a 70% aqueous ethanol solution (15° C.) immediately after solid-liquid separation from the coolant liquid paraffin. Three hours later, the aqueous solution is replaced with the same amount of an 80% aqueous ethanol solution (15° C.), followed by sequential replacements with the same amount of a 90% aqueous ethanol solution (15° C.) and a 99.5% aqueous ethanol solution (15° C.) at 1-hour intervals to remove the water from the capsules. Then, the aqueous solution is replaced with the same amount of 20° C. hexane to remove the coolant liquid adhering to the capsules, after which the capsules are dried at 25° C. for 30 minutes to obtain surfactant-containing seamless capsules having a weight ratio of the surfactant component to the oily component 1:4. The resulting surfactant-containing seamless capsules comprise an inner layer comprising an oily component and a surfactant component, and outermost layer, containing a film-forming material.

Using calipers, the average particle diameter D of the capsules is determined to be 4.2 mm, with a coefficient of variance of 5.9% for particle diameter distribution. The average film thickness t is 0.29 mm, as measured using a micrometer. The water content in the capsules is 3.0% by weight. The film ratio is 25.3% by weight.

Comparative Example 1

Using an apparatus equipped with a double nozzle (the innermost nozzle: inner diameter 0.6 mm and outer diameter 1.0 mm, and outermost nozzle: inner diameter 1.5 mm), multiple-layered droplets are prepared by the following method.

Specifically, a non-aqueous solution (average HLB=10.3) prepared by mixing 90% by weight of tri(caprylic acid captic acid)glycerol (Coconard MT, manufactured by Kao Corporation), 9% by weight of polyoxyethylene (average adduct molar number 20) sorbitan trioleate (HLB=11) and 1% by weight of sorbitan sesquioleate (HLB=3.7), from the innermost nozzle at a flow rate of 7.8 g/min, and an aqueous solution kept at 70° C. comprising 30% by weight of gelatin, 4% by weight of glycerol and 66% by weight of water, from the outermost nozzle at a flow rate of 5 g/min, are simultaneously discharged into a gas phase to form multiple-layered droplets. The resulting droplets are added dropwise to liquid paraffin cooled at 2° C. It has been found, however, that capsules are not formed because the surfactant component in the content liquid is undesirably dispersed in the film-forming liquid, thereby reducing the interfacial tension between the film-forming liquid and the content liquid and that between the film-forming liquid and the coolant liquid.

Comparative Example 2

Seamless capsules are prepared in the same manner as in Example 3 except that the surfactant component is not used.

Using calipers, the average particle diameter D of the capsules is determined to be 5.1 mm, with a coefficient of variance of 6.3% for particle diameter distribution. The average film thickness t is 1.5 mm, as measured using a micrometer. The film ratio is 41.7% by weight.

Comparative Example 3

Using an apparatus equipped with a double nozzle (the innermost nozzle: inner diameter 0.6 mm and outer diameter 1.0 mm, and the outermost nozzle: inner diameter 1.5 mm), multiple-layered droplets are prepared by the following method.

Specifically, a liquid composition prepared by dissolving at 60° C. a mixture comprising 50 g of purified l-carvone, 50 g of octaglycerol monooleate (manufactured by Quest International, trade name: SANTONE 8-1-0) and 20 g of decaglycerol decaoleate (manufactured by Quest International, trade name: SANTONE 10-10-0) and cooling the resulting solution to 30° C., from the innermost nozzle at a flow rate of 1.1 g/min, and an aqueous solution comprising 30% by weight of gelatin, 4% by weight of glycerol and 66% by weight of water, dissolved at 70° C. and then cooled to 45° C., from the outermost nozzle at a flow rate of 1.7 g/min, are simultaneously discharged into a gas phase to form multiple-layered droplets. The resulting droplets are added dropwise to liquid paraffin cooled at 2° C. to obtain capsules having a weight ratio of the surfactant component to the oily component of 7:5. The resulting capsules are surfactant-containing seamless capsules comprising the innermost layer comprising an oily component and a surfactant component, and the outermost layer containing a film-forming material.

After allowing the capsules to stand to dry for 12 hours under the conditions of 5° C. and 20% relative humidity, the average particle diameter D of the capsules is determined to be 4.4 mm, as measured using calipers, with a coefficient of variance of 15.0% for particle diameter distribution. The film thickness t is in the range of 0.35 to 0.75 mm, as measured using a micrometer. The film ratio is 43.9% by weight.

Test Example 1

Figure 2:
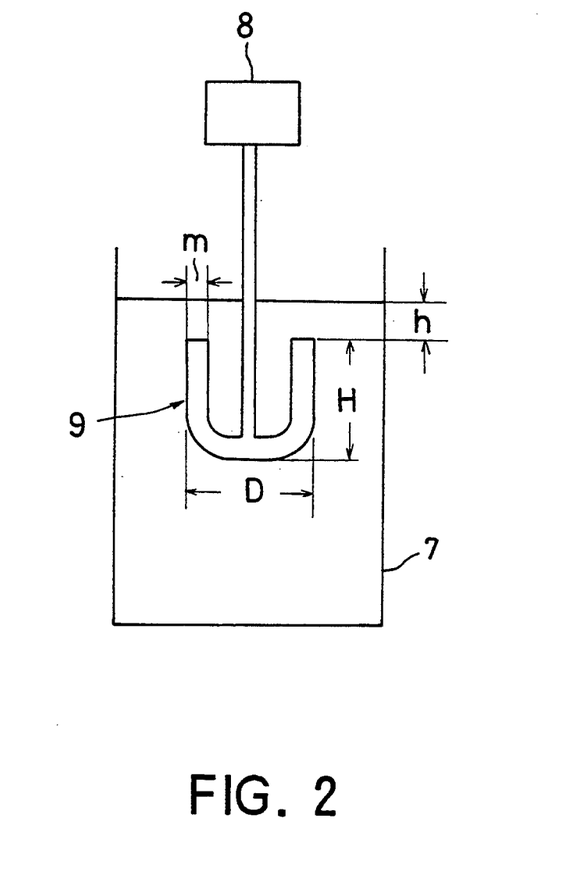
FIG. 2 is a schematic view showing an apparatus for testing emulsifiability in the present invention.

With respect to the capsule liquids content prepared in Examples 1 through 10 and Comparative Examples 2 and 3, the emulsifiability test is carried out by the following method. A schematic view of the testing apparatus is shown in FIG. 2.

Specifically, 0.5 g of the liquid content is added to 2.5 liters of 40° C. water, followed by stirring under the following conditions to emulsify and disperse the oily component in the inner layer. The emulsifiability is observed with the naked eye after emulsive dispersion at 40° C., and after kept standing at 40° C. for 3 hours, 6 hours, and 12 hours, respectively. Stirring conditions:

Container: Three-liter beaker (14 cm inside diameter, 20 cm height);
impeller: Anchor blade (5 cm diameter, 5 cm height, 1 cm width);
Blade position: Upper side of the blade located 1 cm below the water surface level;
Rotational speed of blade: 150 rpm; and Stirring time: 30 seconds.

Here the basis of the evaluation for the emulsification property is as follows:

O: Almost no separation of the emulsion phase, or almost no oil drops freed from the emulsion phase;

Δ: Water phase formation due to emulsion phase separation, or oil drop formation due to emulsion phase separation x: Almost no emulsion phase, and oily component present as free oil drops or oil phase.

The liquids content obtained in Examples 1 through 10 shows no emulsion phase separation, i.e., the oily component remains emulsified and dispersed completely in water at 40° C. after emulsive dispersion and after the liquid content is kept standing at 40° C. for 3, 6 and 12 hours. These liquids content are given the judgment of "o". On the other hand, in the case of the liquid content obtained in Comparative Example 2, containing no surfactant, and the liquid content obtained using a double nozzle in Comparative Example 3, the oily components fail to emulsify or disperse completely in water, with considerable oil floating. These liquid content are given the judgment of "x".

Test Example 2

5 g of a content solution of the capsules obtained in Example 2 g is taken out into a test tube, and kept standing under the conditions of 25° C. and 60% relative humidity for 6 hours. Thereafter, its emulsifiability is observed with the naked eye.

As a result, in the content solution in the test tube, the surfactant component is uniformly dispersed in the oily component.

Formulation Example

A powder comprising 22.00% by weight of sodium hydrogen carbonate, 38.28% by weight of sodium carbonate, 18.00% by weight of succinic acid, 21.00% by weight of PEG 6000, 0.02% by weight of dye and 0.70% by weight of flavor, is heated to 60° C., after which it is granulated using an extrusion granulator. Particles having a diameter between 355 μm and 1400 μm are selectively collected by sieving to prepare a granular bath additive base. To 20 g of this bath additive base, 10 g of the capsules obtained in Example 1 are formulated and mixed to prepare a bath additive composition.

Next, 30 g of the obtained bath additive composition is added to 150 liters of warm water (40° C.). After the solution is stirred ten times with a stirring rod, the dissolution state is observed with the naked eye. No insoluble matter is seen, nor is there any oil floating. The obtained bath additive composition is Thus judged to be excellent in solubility and emulsive dispersibility.

The present invention being thus described, it will be obvious that the same may be varied in many ways. Such variations are not to be regarded as a departure from The spirit and scope of the invention, and all such modifications as would be obvious to one skilled in the art are intended to be included within the scope of the following claims.

What is claimed is:

1. Surfactant-containing seamless capsules comprising an inner layer and an outer layer having a film-forming material, wherein said inner layer comprises a liquid containing an oily component and a surfactant component, and wherein the emulsifiability of said liquid in the capsules is such that when 0.5 g. of said liquid is added to 2.5 liters of 40° C. water, followed by stirring under the conditions shown below, the oily component remains emulsified and dispersed and substantially unseparated from the water at 40° C.:

Stirring conditions:

| Container: | Three-liter beaker (14 cm inside diameter, 20 cm height); |
|---|---|
| Impeller: | Anchor blade (5 cm diameter, 5 cm height, 1 cm width); |
| Blade position: | Upper side of the blade located 1 cm below the water surface level; |
| Rotational speed of blade: | 150 rpm; and |
| Stirring time: | 30 seconds. |

2. Surfactant-containing seamless capsules comprising an inner layer and an outer layer having a film-forming material, wherein said inner layer contains oily component and a surfactant component, said surfactant component being substantially uniformly dispersed or dissolved in the oily component.

3. The surfactant-containing seamless capsules according to claim 2, wherein the emulsifiability of the liquid content in the inner layer of the capsules is such that when 0.5 g of the liquid is added to 2.5 liters of 40° C. water, followed by stirring under the conditions shown below the oily component remains emulsified and dispersed and substantially unseparated from the water at 40° C.:

Stirring conditions:

| Container: | Three-liter beaker (14 cm inside diameter, 20 cm height); |
|---|---|
| Impeller: | Anchor blade (5 cm diameter, 5 cm height, 1 cm width); |
| Blade position: | Upper side of the blade located 1 cm below the water surface level; |
| Rotational speed of blade: | 150 rpm; and |
| Stirring time: | 30 seconds. |

4. The surfactant-containing seamless capsules according to claim 1, wherein the weight ratio of the film based on the weight of the capsules is 5 to 60%.

5. The surfactant-containing seamless capsules according to claim 1, wherein the average particle diameter of the capsules is 0.2 mm to 2 cm.

6. The surfactant-containing seamless capsules according to claim 1, wherein the capsules comprise an inner layer having a concentric layered structure of two or more sublayers, and an outer layer of a film-forming material, said inner layer having one of the structures selected from the group consisting of (A), (B), (C) and (D) of the following:

(A) at least one of the sublayers comprising an aqueous dispersion containing an oil component and a surfactant component;

(B) at least one of the sublayers comprising an aqueous dispersion containing an oil component, a surfactant component and a hydrophilic organic solvent;

(C) at least one of the sublayers comprising a non-aqueous liquid comprising an oil component and a surfactant component; and (D) at least one of the sublayers comprising a surfactant component.

7. The surfactant-containing seamless capsules according to claim 1, wherein said surfactant is a nonionic surfactant having an HLB value of 7 to 18.

8. The surfactant-containing seamless capsules according to claim 7, wherein said nonionic surfactant is selected from the group consisting of sorbitan fatty acid esters, polyoxyethylenesorbitan fatty acid esters, polyoxyethylenesorbitol fatty acid esters, and mixtures thereof.

9. The surfactant-containing seamless capsules according to claim 1, wherein a component of the film-forming material is selected from the group consisting of natural hydrophilic polymers, semi-synthetic hydrophilic polymers, synthetic hydrophilic polymers and mixtures thereof.

10. The surfactant-containing seamless capsules according to claim 1, wherein the film-forming material comprises a compound selected from the group consisting of glue, gelatin, collagen protein, casein, sodium alginate, carrageenan, furcelan, tamarind gum, pectin, gum arabic, guar gum, xanthane gum, tragacanth gum, locust bean gum, agar, starch, carboxymethyl cellulose, methyl cellulose, hydroxyethyl cellulose, hydroxypropyl cellulose, cellulose acetate phthalate, alginic acid propylene glycol ester, oxidized starch, esterified starch, etherified starch, cationized starch, sodium polyacrylate, polyethyleneimine, poll;vinyl alcohol, polyethylene oxide, polyvinylpyrrolidone, and mixtures thereof.

11. The surfactant-containing seamless capsules according to claim 1, wherein said outer layer further comprises a water-soluble polyhydric alcohol, a derivative thereof, or a mixture thereof.

12. The surfactant-containing seamless capsules according to claim 11, wherein said water-soluble polyhydric alcohol or derivative thereof is selected from the group consisting of glycerol, sorbitol, ethylene glycol, polyethylene glycol, propylene glycol, polypropylene glycol, ethylene oxide-propylene oxide copolymer, oligosaccharides, glycerides, and mixtures thereof.

* * * * *